United States Patent [19]

Rose et al.

[11] Patent Number: 4,698,066
[45] Date of Patent: Oct. 6, 1987

[54] AMINE OXIDATION DYE HAIR TREATING COMPOSITIONS

[75] Inventors: David Rose, Hilden; Norbert Maak, Neuss; Edgar Lieske, Duesseldorf, all of Fed. Rep. of Germany

[73] Assignee: Henkel Kommanditgesellschaft auf Aktien, Duesseldorf, Fed. Rep. of Germany

[21] Appl. No.: 841,901

[22] Filed: Mar. 20, 1986

[30] Foreign Application Priority Data

Mar. 20, 1985 [DE] Fed. Rep. of Germany ....... 3510039

[51] Int. Cl.$^4$ ...................... A61K 7/13; C07C 143/56; C07C 101/48
[52] U.S. Cl. .......................................... 8/408; 8/410; 8/412; 8/416; 260/508; 562/456; 562/457
[58] Field of Search .................. 8/412, 410, 416, 408; 260/508; 562/457, 456

[56] References Cited

U.S. PATENT DOCUMENTS

| | | | |
|---|---|---|---|
| 3,415,608 | 12/1968 | Tucker | 8/10.2 |
| 3,488,138 | 1/1970 | Iscowitz | 8/10.1 |
| 3,861,868 | 1/1975 | Milbrada | 8/10.2 |
| 4,104,021 | 8/1978 | Lapidus et al. | 8/10.2 |
| 4,112,229 | 9/1978 | Kalopissis et al. | 544/105 |
| 4,200,432 | 4/1980 | Kalopissis et al. | 8/408 |

FOREIGN PATENT DOCUMENTS

| | | |
|---|---|---|
| 179881 | 6/1905 | Fed. Rep. of Germany . |
| 163645 | 10/1905 | Fed. Rep. of Germany . |
| 294184 | 9/1916 | Fed. Rep. of Germany . |
| 1444216 | 10/1962 | Fed. Rep. of Germany . |
| 2132214 | 3/1972 | France . |
| 2352542 | 5/1977 | France . |
| 270075 | 5/1927 | United Kingdom . |

OTHER PUBLICATIONS

Bently, R. K. et al., "Pigments of Pseudomonas Species," *Journal of the Chemical Society*, (Eng)(C), 1970, v18, pp. 2447-2457.

Journal fur Praktische Chemie (2), 91 (1915), pp. 202-212.

*Primary Examiner*—Paul Lieberman
*Assistant Examiner*—Linda Skaling
*Attorney, Agent, or Firm*—Ernest G. Szoke; Henry E. Millson, Jr.; Mark A. Greenfield

[57] ABSTRACT

A hair treating composition containing certain substituted aminodiphenylamines as a first oxidation dye precursor, optionally at least one second oxidation dye precursor, optionally at least one substantive hair dye, and a cosmetic carrier; as well as a method for its use.

34 Claims, No Drawings

AMINE OXIDATION DYE HAIR TREATING COMPOSITIONS

BACKGROUND OF THE INVENTION

1. Field of the Invention

This invention relates to hair treating compositions containing amine oxidation dye precursors such as developers and/or couplers.

2. Statement of the Related Art

Some hair treatment compositions used in hair dyeing contain oxidation dye precursors in a cosmetic carrier. The oxidation dye precursors used are developers and couplers which together form dyes by oxidative coupling with one another under the influence of oxidizing agents or atmospheric oxygen. The cosmetic carriers used for the oxidation dye precursors are creams, emulsions, gels, shampoos, foam aerosols or other preparations suitable for application to the hair.

By virtue of their intensive colors and good fastness properties, oxidation dyes, which are formed by the oxidative coupling of one or more developer components with one another or with one or more coupler components, play a prominent part in the dyeing of hair. The developer components used are normally primary aromatic amines containing additionally a free or substituted hydroxy or amine moiety in the para or ortho position, diaminopyridine derivatives, heterocyclic hydrazone derivatives, 4-aminopyrazolone derivatives and tetraaminopyrimidines. Useful couplers include m-phenylene diamine derivatives, naphthols, resorcinol derivatives and pyrazolones.

Good oxidation dye precursors have to satisfy above all the following requirements: (1) they must form the required shades with sufficient intensity and fastness during the oxidative coupling reaction; (2) they must be readily absorbed by human hair without excessively staining the scalp; and (3) they must be safe to use, above all from the toxicological and dermatological viewpoint.

Although p-phenylene diamine and several of its derivatives have long been known as oxidation dye precursors, it is also known that many of these compounds are neither toxicologically nor dermatologically safe because they show mutagenic and/or allergenic properties. Accordingly, there is considerable commercial interest in oxidation dye precursors which, on the one hand, produce intensive colors characterized by high fastness properties, and which on the other hand, are both toxicologically and dermatologically safe.

DESCRIPTION OF THE INVENTION

Other than in the operating examples, or where otherwise indicated, all numbers expressing quantities of ingredients, reaction conditions, or defining ingredient parameters used herein are to be understood as modified in all instances by the term "about".

It has now been found that hair dyes which contain certain first oxidation dye precursors (i.e. first couplers) in a cosmetic carrier and which contain second oxidation dye precursors (i.e. developer components and optionally second coupler components) normally used in oxidation dyes, satisfy the requirements stated above to a high degree and are safe to use, particularly in respect of their toxicological and dermatological properties.

The (first) oxidation dye precursor (i.e. coupler) useful in the hair treating compositions of this invention is at least one aminodiphenylamine corresponding to the following general formula or its water soluble salt:

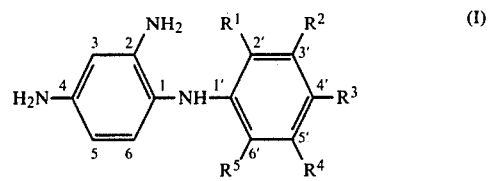

wherein:
(a) one of $R^1$ to $R^5$ is $-SO_3H$, $-COOH$, or $-CH_2-COOH$;
(b) from 2 to 4 of $R^1$ to $R^5$ are H; and
(c) the remaining of $R^1$ to $R^5$ are independently $C_{1-4}$-alkyl, $C_{1-4}$-alkoxy, or Cl.

In the above formula I, preferred embodiments are wherein:
(a) one of $R^1$ to $R^5$ is $-SO_3H$ or $-COOH$;
(b) 3 or 4 of $R^1$ to $R^5$ is H; and
(c) the remaining one of $R^1$ to $R^5$ (if any) is methyl ($C_1$-alkyl) or Cl, most preferably methyl.

The aminodiphenylamines corresponding to formula I may be introduced into the hair treating compositions according to the invention in free form (or in the form of their inner salts) or in the form of: (a) salts of the amino groups with inorganic or organic acids, for example in the form of the hydrochlorides, sulfates, phosphates, acetates, propionates, lactates or citrates; or (b) in the form of salts of the $-SO_3H$, $-COOH$ and/or $-CH_2-COOH-$ group, for example the ammonium salts or the alkali metal (especially sodium) salts.

The aminodiphenylamines corresponding to formula I are suitable as couplers for a number of known developers and produce particularly brilliant dye finishes characterized by high heat and light stability and by high stability to permanent-wave treatment. Particular emphasis is placed on the especially attractive brown tones, which approach the natural color of hair, and which are obtained with developers of the aromatic diamine type.

Some of the compounds corresponding to formula I are known from the literature. Those compounds having this structure which are not known from the literature can be produced by methods known per se. Thus, 2,4,-diaminodiphenylamine-4'-sulfonic acid for example is disclosed in German Pat. No. 163,645. The production of 2,4,-diamino-4'-carboxydiphenylamine and 2,4-diamino-3'-carboxydiphenylamine is described in Journ. Prakt. Chem. (2) 91 (1915), pages 202-212. In general, aminodiphenylamines corresponding to formula I may be obtained by reaction of an aminobenzene derivative corresponding to the following formula

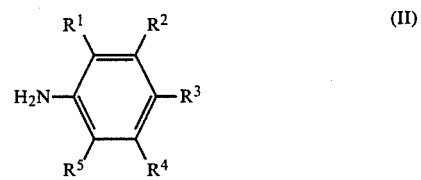

in which the groups $R^1$ to $R^5$ have the meanings defined for formula I, with 2,4-dinitrofluorobenzene and catalytic hydrogenation of the 2,4-dinitrodiphenylamines thus obtained to form the corresponding 2,4-diaminophenylamines. Some examples of the production of aminodiphenylamines which are believed to be novel are described in the examples which follow.

The developer (second oxidation dye precursor) components in the hair dyes according to the invention include aromatic amines containing one or more other $NH_2$-groups, $NHR$-groups, or $NR_2$-groups, where R is: a $C_{1-4}$-alkyl group; a $C_{2-4}$ hydroxyalkyl group; an amino-$C_{2-4}$-alkyl group; aminophenols; aminophenolethers; diaminopyridine derivatives; or 2,4,5,6-tetraminopyrimidine and derivatives thereof, such as
4,5-diamino-2,6-bismethylaminopyrimidine,
2,5-diamino-4-diethyamino-6-methylaminopyrimidine,
2,4,5-triamino-6-anilinopyrimidine,
2,4,5-triamino-6-morpholinopyrimidine,
2,4,5-triamino-6-(2-hydroxyethyl)-aminopyrimidine.

Particularly intense and natural brown to gray shades are obtained where the new couplers are used in oxidation dyes together with developers of the aromatic diamine type and more particularly of the p-phenylene diamine derivative type.

Preferred developers of this type include
p-phenylene diamine,
p-tolylene diamine,
N-methyl-p-phenylene diamine,
N,N-dimethyl-p-phenylene diamine,
N-hydroxyethyl-p-phenylene diamine,
N,N-bis-(2-hydroxyethyl)-p-phenylene diamine,
N-ethyl-N-(2-hyroxyethyl)-p-phenylene diamine,
N,N-diethyl-2-methyl-p-phenylene diamine,
2-chloro-p-phenylene diamine,
2,6-dichloro-p-phenylene diamine,
2-chloro-6-methyl-p-phenylene diamine,
2-methoxy-p-phenylene diamine,
2,5-diaminoanisole,
6-methoxy-3-methyl-p-phenylene diamine,
N-(2-methoxyethyl)-p-phenylene diamine,
N-(2-hydroxypropyl)-p-phenylene diamine,
N-butyl-N-sulfobutyl-p-phenylene diamine,
N-(p-aminophenyl)-N',N'-bis-($\beta$hydroxyethyl)-1,3-diaminopropane or salts thereof with inorganic or organic acids.

In addition to the aminodiphenylamines corresponding to general formula I, the hair dyes according to the invention may also contain known other (second) couplers or oxidation dye precursors which are necessary for modifying the shades and for producing natural colors. Known second coupler compounds of the type in question include other n-phenylene diamines, for example 2,4-diaminophenyl-2-hydroxyethylether, 2,4-diaminoanisole or phenols, resorcinols, m-aminophenols, naphthols or pyrazolones.

Substantive dyes may also be additionally used for further modifying the shades. Useful substantive dyes include nitrophenylene diamines, nitroaminophenols, anthraquinone dyes or indophenols.

The aminodiphenylamines (first couplers or precursors) corresponding to formula I and the second coupler compounds additionally present, if any, are generally used in substantially equimolar quantities, based on the developer compounds employed. A certain excess of individual oxidation dye precursors is not a disadvantage, so that first and second precursors may be present in respective molar ratios of 1:0.5–2.

There is no need for the aminodiphenylamines corresponding to formula I and the second oxidation dye precursors or substantive dyes otherwise present in the hair dyes to be separate chemical compounds. On the contrary, they may even be mixtures of the couplers or developers used in accordance with the invention.

In principle, the oxidative development of the dye may be carried out with atmospheric oxygen. However, it is preferred to use a chemical oxidizing agent, particularly when it is desired to lighten as well as color the hair. Suitable oxidizing agents are, in particular, hydrogen peroxide or adducts thereof with urea, melamine or sodium borate and also mixtures of hydrogen peroxide adducts such as these with potassium peroxide disulfate.

To produce the hair dyes according to the invention, the first, or first and second oxidation dye precursors are incorporated in a suitable cosmetic carrier in an amount sufficient to form an effective hair dye upon oxidation coupling. Examples of suitable cosmetic carriers are creams, emulsions, lotions, gels, foam aerosols, or even surfactant-containing foaming solutions, for example shampoos, or other preparations which are suitable for applications to the hair. Standard ingredients of cosmetic preparations such as these are: wetting agents and emulsifiers, such as anionic, nonionic or ampholytic surfactants, for example fatty alcohol sulfates, alkane sulfonates, alpha-olefin sulfonates, fatty alcohol polyglycol ether sulfates, ethylene oxide adducts with fatty alcohols, fatty acids or alkylphenols, sorbitan fatty acid esters and fatty acid partial glycerides, fatty acid alkanolamides, thickeners, such as methyl or hydroxyethyl cellulose, starch, fatty alcohols, paraffin oils, fatty acids, perfume oils and hair-care additives, such as water-soluble cationic polymers, protein derivatives, pantothenic acid and cholesterol, and inhibitors such as $Na_2SO_3$.

The ingredients of the cosmetic carriers are used in the usual quantities in the production of the hair dyes according to the invention. For example, the emulsifiers are used in concentrations of from 0.5 to 30% by weight (w/w) and the thickeners in concentrations of from 0.1 to 25% by weight, based on the formulation as a whole. The combined oxidation dye precursors are preferably incorporated in the carrier in total quantities of from 0.2 to 5% by weight and most preferably in quantities of from 1 to 3% by weight, based on the formulation as a whole. The aminodiphenylamines corresponding to formula I (first coupler or first oxidation dye precursor) are preferably present in the hair dyes according to the invention in quantities of from about 0.05 to 10, most preferably 7 to 8, millimoles per 100 g of the total composition, which is preferably aqueous.

The hair dyes according to the invention may be used in a mildly acidic, neutral or alkaline medium, irrespective of the cosmetic carrier used. The hair dyes are preferably adjusted to a pH-range of 8 to 10. They may be used at temperatures of from 15° C. to 40° C., preferably 25° C. to 30° C. After a contact time of around 20 to 40, preferably about 30 minutes, the hair dye is removed by rinsing from the hair to be dyed, preferably with water. The hair is then washed with a mild shampoo and dried. Washing with a shampoo is unnecessary when a carrier of high surfactant content, for example a dye shampoo, is used. The hair dyes of this invention are primarily intended for the treatment of human hair. It is possible, however, to use the dyes for non-human hair, fur, and the like, if desired.

The following Examples are intended to illustrate but not limit the invention.

EXAMPLES

1. Preparation of typical aminodiphenylamines corresponding to formula I

1.1 2,4-diaminodiphenylamine-2'-sulfonic acid, Na salt

1st step

A mixture of 17.3 g (0.1 mol) of: o-sulfanilic acid, 4.0 g (0.1 mol); sodium hydroxide, 8.2 g (0.1 mol); $CH_3COONa$, 12.6 g (0.1 mol); and 2,4-dinitrofluorobenzene in 100 ml of water was boiled under reflux for 3 hours. After cooling, the reaction product was filtered off and dried in vacuo at 80° C. A 2,4-dinitrodiphenylamine-2'-sulfonic acid sodium salt melting at 274° C. (with decomposition) was obtained in a yield of 29.5 g (74% of the theoretical).

2nd step 6.0 g of the above 2,4-dinitrodiphenylamine-2'-sulfonic acid sodium salt were dissolved in 250 ml of ethanol and, after the addition of 0.5 g of an active carbon containing 5% by weight palladium, the resulting solution was hydrogenated in a hydrogen atmosphere. After hydrogen had stopped being taken up, the catalyst was removed and the solution concentrated to dryness. Pink-colored crystals melting above 225° C. were obtained.

1.2 2,4-diaminodiphenylamine-3'-sulfonic acid, Na salt

Starting from m-sulfanilic acid, the 2,4-dinitrodiphenylamine-3'-sulfonic acid sodium salt was obtained in the form of orange-colored crystals melting at 195° C. (with decomposition) by the method described in 1.1. The 2,4-diaminodiphenylamine-3'-sulfonic acid sodium salt in the form of beige crystals melting beyond 175° C. (with decomposition) was obtained therefrom by catalytic hydrogenation as in 1.1.

1.3 2,4-diamino-4'-methyldiphenylamine-2'-sulfonic acid, Na salt

Starting from 6-amino-m-toluene sulfonic acid, the 2,4-dinitro-4'-methyldiphenylamine-2'-sulfonic acid sodium salt was obtained in the form of orange-colored crystals melting above 250° C. by the method described in 1.1. The 2,4-diamino-4'-methyldiphenylamine-2'-sulfonic acid sodium salt in the form of red crystals melting above 250° C. was obtained therefrom by catalytic hydrogenation.

1.4 2,4-diaminodiphenylamine-4'-sulfonic acid, Na salt

1st step

A mixture of 18.6 g (0.1 mol) of 2,4-dinitrofluorobenzene, 17.3 g (0.1 mol) of p-sulfanilic acid, 4 g (0.1 mol) of sodium hydroxide and 8.2 g (0.1 mol) of sodium acetate was refluxed for 3 hours in 100 ml of water. After cooling to 20° C., the reaction product was filtered off and dried in vacuo at 80° C. The 2,4-dinitrodiphenylamine-4'-sulfonic acid sodium salt obtained melted at around 285° C. (with decomposition).

2nd Step 6 g of the above 2,4-dinitrodiphenylamine-4'-sulfonic acid sodium salt was dissolved in a mixture of 250 ml of ethanol and 50 ml of water and, after the addition of 0.5 g of an active carbon containing 5% by weight of palladium, the resulting solution was hydrogenated in a hydrogen atmosphere. After hydrogen had stopped being taken up, the catalyst was removed by filtration and the filtrate concentrated to dryness. A 2,4-diaminodiphenylamine-4'-sulfonic acid sodium salt was obtained in the form of pink-colored crystals melting above 310° C.

1.5 2,4-diamino-2'-carboxy-4'-methyldiphenylamine trihydrochloride

1st Step

A mixture of 9.4 g (0.05 mol) of 2,4-dinitrofluorobenzene, 7.7 g (0.05 mol) of 2-amino-5-methylbenzoic acid, 6.0 g (0.005 mol) of $Na_2CO_3$ in 100 ml of a mixture of ethanol and water (1:1) was stirred for 3 hours at 40° C. After cooling to +10° C., the reaction product was filtered off, washed with ethanol and dried in vacuo at 60° C. Red crystals melting above 250° C. were obtained in a quantity of 15.6 g (yield 91% of the theoretical).

2nd Step

The 2,4-dinitro-2'-carboxy-4'-methyldiphenylamine sodium salt (from the 1st step) was dissolved in 500 ml of ethanol and, after the additional of 1 g of an active carbon charged with 5% by weight palladium, the resulting solution was hydrogenated in a hydrogen atmosphere. After the hydrogen was taken up, the catalyst removed by filtration and the filtrate acidified with concentrated hydrochloric acid. After concentration, 2,4-diamino-2'-carboxy-4'-methyldiphenylamine trihydrochloride in the form colorless crystals melting at 220° to 225° C. (with decomposition) was obtained in a quantity of 10.2 g.

1.6 2,4-diamino-3'-carboxy-6'-methyldiphenylamine trihydrochloride

Starting from 3-amino-4-methylbenzoic acid, the 2,4-dinitro-3'-carboxy-6'-methyldiphenylamine sodium salt was obtained in the form of orange-colored crystals melting at 187° C. (with decomposition) by the method described in 1.4. The 2,4-diamino-3'-carboxy-6'-methyldiphenylamine tetrahydrochloride in the form of gray crystals melting at 249° C. (with decomposition) was obtained therefrom by catalytic hydrogenation.

1.7 2,4-diamino-3'-carboxy-6'-methoxydiphenylamine dihydrochloride dihydrate Starting from 3-amino-4-methoxybenzoic acid, the 2,4-dinitro-3'-carboxy-6'-methoxydiphenylamine sodium salt was obtained in the form of orange-colored crystals melting above 250° C. by the method described in 1.4. The 2,4-diamino-3'-carboxy-6'-methoxydiphenylamine dihydrochloride dihydrate in the form of gray crystals melting at 249° C. (with decomposition) was obtained therefrom by hydrogenation.

1.8 2,4-diamino-2'-carboxy-6'-methyldiphenylamine trihydrochloride dihydrate Starting from 2-amino-3-methylbenzoic acid, the 2,4-dinitro-2'-carboxy-6'-methyldiphenylamine sodium salt was obtained in the form of orange-colored crystals melting above 250° C. by the method described in 1.4. The 2,4-diamino-2'-carboxy-6'-methyldiphenylamine trihydrochloride dihydrate in the form of red crystals melting at 234° C. (with decomposition) was obtained therefrom by catalytic hydrogenation.

1.9 2,4-diamino-2'-carboxy-3'-methyldiphenylamine trihydrochloride dihydrate Starting from 2-amino-6-methylbenzoic acid, the 2,4-dinitro-2'-carboxy-3'-methyldiphenylamine sodium salt was obtained in the form of red crystals melting above 250° C. (with decomposition) by the method described in 1.4. The 2,4-diamino-2'-carboxy-3'-methyldiphenylamine trihydrochloride dihydrate in the form of a colorless powder melting at 213° C. (with decomposition) was obtained therefrom by catalytic hydrogenation.

1.10 2,4-diamino-2'-carboxy-5'-chlorodiphenylamine trihydrochloride dihydrate Starting out from 2-amino-4-chlorobenzoic acid, the 2,4-dinitro-2'-carboxy-5'-chlorodiphenylamine sodium salt was obtained in the form of red crystals melting above 250° C. (with decomposition) by the method described in 1.4. The 2,4-diamino-2'-carboxy-5'-chlorodiphenylamine trihydrochloride dihydrate in the form of a gray powder melting at 249° C. (with decomposition) was obtained therefrom by catalytic hydrogenation (in the presence of Raney nickel).

1.11 2,4-diamino-4'-carboxymethyldiphenylamine dihydrochloride

1st Step

A mixture of 7.6 g (0.05 mol) of p-aminophenylacetic acid and 10 g (0.12 mol) of $NaHCO_3$ in 60 ml of ethanol was heated to 50° C., followed by dropwise addition of 9.3 g (0.05 mol) of 2,4-dinitrofluorobenzene. After 3 hours' boiling under reflux, the reaction product was filtered off and dried in vacuo at 80° C. 2,4-dinitro-4'-carboxymethyldiphenylamine Na salt in the form of orange-colored crystals melting at 206° C. (with decomposition) was obtained in a quantity of 14.7 g (yield 93% of the theoretical).

2nd Step

The 2,4-dinitro-4'-carboxymethyldiphenylamine Na salt obtained above was hydrogenated as in 1.4 (2nd step). A 2,4-diamino-4'-carboxylmethyldiphenylamine dihydrochloride was obtained in the form of pink crystals melting beyond 180° C. (with decomposition).

2. Performance tests

Hair dyes according to the invention were prepared in the form of a hair dye cream emulsion having the following composition:

| | |
|---|---|
| $C_{12-14}$ fatty alcohol | 10 g |
| $C_{12-14}$ fatty alcohol + 2 E.O. sulfate, Na salt, 28% | 25 g |
| Water | 60 g |
| Coupler | 7.5 millimoles |
| Developer | 7.5 millimoles |
| $Na_2SO_3$ (inhibitor) | 1.0 g |
| Concentrated ammonia solution | to pH = 9.5 |
| Water q.s. to | 100 g |

The constituents were mixed together in the above order. After addition of the coupler, developer, and the inhibitor, the pH value of the emulsion was first adjusted to 9.5 with concentrated ammonia solution, after which the emulsion was made up with water to 100 g.

Oxidative development of the dye was carried out with 3% hydrogen peroxide solution as the oxidizing agent. To this end, 50 g of hydrogen peroxide solution (3%) were added to and mixed with 100 g of the emulsion.

The dyeing cream was applied to approximately 5 cm long strands of standardized, 90% gray, but not specially pretreated, human hair and left thereon for 30 minutes at 27° C. After dyeing, the hair was rinsed, washed with a standard shampoo and then dried.

The following compounds were used as couplers (precursor 1):

TABLE 1

| Coupler | Formula | Corresponding Example |
|---|---|---|
| C 1 | 2,4-diaminodiphenylamine-4'-sulfonic acid, Na salt | 1.4 |
| C 2 | 2,4-diaminodiphenylamine-2'-sulfonic acid, Na salt | 1.1 |
| C 3 | 2,4-diaminodiphenylamine-3'-sulfonic acid, Na salt | 1.2 |
| C 4 | 2,4-diamino-4'-methyldiphenylamine-2'-sulfonic acid, Na salt | 1.3 |
| C 5 | 2,4-diamino-4'-carboxydiphenylamine | — |
| C 6 | 2,4-diamino-3'-carboxydiphenylamine | — |
| C 7 | 2,4-diamino-2'-carboxy-3'-methyldiphenylamine | 1.9* |
| C 8 | 2,4-diamino-3'-carboxy-6'-methyldiphenylamine | 1.6* |
| C 9 | 2,4-diamino-2'-carboxy-6'-methyldiphenylamine | 1.8* |
| C 10 | 2,4-diamino-2'-carboxy-4'-methyldiphenylamine | 1.5* |
| C 11 | 2,4-diamino-2'-carboxy-6'-methoxydiphenylamine | 1.7* |
| C 12 | 2,4-diamino-2'-carboxy-5'-chlorodiphenylamine | 1.10* |

*salt not specified

The following compounds were used as developers (precursor 2):

TABLE 2

| Developer | Formula |
|---|---|
| D 1 | p-tolylene diamine |
| D 2 | N—(2-hydroxyethyl)-p-phenylene diamine |
| D 3 | N—N—bis-(2-hydroxyethyl)-p-phenylene diamine |
| D 4 | N—ethyl-N—(2-hydroxyethyl)-p-phenylene diamine |
| D 5 | N,N—diethyl-p-phenylene diamine |
| D 6 | 2-chloro-p-phenylene diamine |
| D 7 | N—benzyl-p-phenylene diamine |
| D 8 | N—(p-aminophenyl)-N',N'—bis-(2-hydroxyethyl)-1,3-diaminopropane |
| D 9 | 2,5-diaminoanisole |
| D 10 | 2,5-diaminopyridine |
| D 11 | p-aminophenol |
| D 12 | 2,4,5,6-tetraaminopyrimidine |
| D 13 | 6-piperidino-2,4,5-triaminopyrimidine |

Various combinations of the above couplers and developers were formulated into hair dye cream emulsions in accordance with the foregoing description. All resulted in acceptable hair coloration, and the results are given in the following table.

| Application Example No. | Coupler | Developer | Color of the dyed hair strands |
|---|---|---|---|
| 2.1 | C 1 | D 1 | dark olive-brown |
| 2.2 | C 1 | D 5 | brown-gray |
| 2.3 | C 1 | D 11 | fawn |
| 2.4 | C 1 | D 12 | olive-brown |
| 2.5 | C 2 | D 1 | dark brown |
| 2.6 | C 2 | D 3 | brown-gray |
| 2.7 | C 2 | D 7 | gray-brown |
| 2.8 | C 2 | D 11 | fawn |
| 2.9 | C 2 | D 12 | olive-green |
| 2.10 | C 3 | D 1 | dark brown |
| 2.11 | C 4 | D 1 | brown |
| 2.12 | C 5 | D 1 | dark brown |

-continued

| Application Example No. | Coupler | Developer | Color of the dyed hair strands |
|---|---|---|---|
| 2.13 | C 6 | D 1 | black-brown |
| 2.14 | C 7 | D 1 | dark brown |
| 2.15 | C 8 | D 1 | dark brown |
| 2.16 | C 9 | D 1 | dark brown |
| 2.17 | C 9 | D 4 | red-gray |
| 2.18 | C 9 | D 12 | dark green |
| 2.19 | C 9 | D 13 | light brown |
| 2.20 | C 10 | D 1 | dark brown |
| 2.21 | C 10 | D 2 | violet-gray |
| 2.22 | C 10 | D 6 | gray-brown |
| 2.23 | C 10 | D 9 | purple-gray |
| 2.24 | C 10 | D 11 | chocolate brown |
| 2.25 | C 10 | D 12 | dark green |
| 2.26 | C 11 | D 1 | brown |
| 2.27 | C 11 | D 2 | blue-gray |
| 2.28 | C 11 | D 8 | violet-gray |
| 2.29 | C 11 | D 10 | red-brown |
| 2.30 | C 11 | D 12 | olive brown |
| 2.31 | C 12 | D 1 | black-brown |

We claim:

1. In an oxidative dye hair treating composition containing at least one first oxidation dye precursor, optionally at least one substantive hair dye, and a cosmetic carrier, the improvement wherein
said at least one first oxidation dye precursor is a coupler which is present in an amount sufficient to form an effective hair dye upon oxidation coupling, and consists essentially of a compound of the following formula, or a water soluble salt thereof:

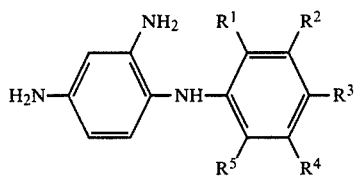

wherein:
(a) one of $R^1$ to $R^5$ is —SO$_3$H, —COOH, or —CH$_2$—COOH;
(b) from 2 to 4 $R^1$ to $R^5$ are H; and
(c) the remaining of $R^1$ to $R^5$ are independently $C_{1-4}$-alkyl, $C_{1-4}$-alkoxy, or Cl; and
a second oxidation dye precursor comprising at least one developer which is a compound other than said first oxidation dye precursor is present in a first:second oxidation dye precursor mol ratio of 1:0.5–2.0.

2. The composition of claim 1 wherein:
(b) from 3 to 4 of $R^1$ to $R^5$ are H; and
(c) the remaining of $R^1$ to $R^5$ are independently methyl, methoxy, or Cl.

3. The composition of claim 2 wherein:
(a) one of $R^1$ to $R^5$ is —SO$_3$H or —COOH;
(b) three of $R^1$ to $R^5$ are H; and
(c) the remaining one of $R^1$ to $R^5$ is methyl.

4. The composition of claim 2 wherein:
(a) one of $R^1$ to $R^5$ is —SO$_3$H, or —COOH; and
(b) the remaining four of $R^1$ to $R^5$ are H.

5. The composition of claim 1 wherein said first oxidation dye precursor is in the form of a salt of at least one amino group present in said formula with inorganic or organic acids.

6. The composition of claim 5 wherein said salt is at least one hydrochloride, sulfate, phosphate, acetate, propionate, lactate, or citrate.

7. The composition of claim 1 wherein said first oxidation dye precursor is in the form of an ammonium or alkali metal salt of the —SO$_3$H, —COOH, or —CH$_2$—COOH group present in said formula.

8. The composition of claim 1 wherein said first oxidation dye precursor is present in its free form.

9. The composition of claim 1 wherein said second oxidation dye precursor additionally comprises a coupler other than the first oxidation dye precursor.

10. The composition of claim 1 wherein wherein said second oxidation dye precursor is at least one of:
p-tolylene diamine;
N-(2-hydroxyethyl)-p-phenylene diamine;
N-N-bis-(2-hydroxyethyl)-p-phenylene diamine;
N-ethyl-N-(2-hydroxyethyl)-p-phenylene diamine;
N,N-diethyl-p-phenylene diamine;
2-chloro-p-phenylene diamine;
N-benzyl-p-phenylene diamine;
N-(p-aminophenyl)-N',N'-bis-(2-hydroxyethyl)-1,3-diaminopropane;
2,5-diaminoanisole;
2,5-diaminopyridine;
p-aminophenol;
2,4,5,6-tetraaminopyrimidine; or
6-piperidino-2,4,5-triaminopyrimidine.

11. The composition of claim 1 wherein said first oxidation dye precursor is at least one of:
2,4-diaminodiphenylamine-4'-sulfonic acid, Na salt;
2,4-diaminodiphenylamine-2'-sulfonic acid, Na salt;
2,4-diaminodiphenylamine-3'-sulfonic acid, Na salt;
2,4-diamino-4'-methyldiphenylamine-2'-sulfonic acid, Na salt;
2,4-diamino-4'-carboxydiphenylamine;
2,4-diamino-3'-carboxydiphenylamine;
2,4-diamino-2'-carboxy-3'-methyldiphenylamine;
2,4-diamino-3'-carboxy-6'-methyldiphenylamine;
2,4-diamino-2'-carboxy-6'-methyldiphenylamine;
2,4-diamino-2'-carboxy-4'-methyldiphenylamine;
2,4-diamino-3'-carboxy-6'-methoxydiphenylamine; or
2,4-diamino-2'-carboxy-5'-chlorodiphenylamine.

12. The composition of claim 10 wherein said first oxidation dye precursor is at least one of:
2,4-diaminodiphenylamine-4'-sulfonic acid, Na salt;
2,4-diaminodiphenylamine-2'-sulfonic acid, Na salt;
2,4-diaminodiphenylamine-3'-sulfonic acid, Na salt;
2,4-diamino-4'-methyldiphenylamine-2'-sulfonic acid, Na salt;
2,4-diamino-4'-carboxydiphenylamine;
2,4-diamino-3'-carboxydiphenylamine;
2,4-diamino-2'-carboxy-3'-methyldiphenylamine;
2,4-diamino-3'-carboxy-6'-methyldiphenylamine;
2,4-diamino-2'-carboxy-6'-methyldiphenylamine;
2,4-diamino-2'-carboxy-4'-methyldiphenylamine;
2,4-diamino-3'-carboxy-6'-methoxydiphenylamine; or
2,4-diamino-2'-carboxy-5'-chlorodiphenylamine.

13. The composition of claim 11 wherein said second oxidation dye precursor is present and the mol ratio of first to second oxidation dye precursor is about equimolar.

14. The composition of claim 10 wherein said second oxidation dye precursor is present and the mol ratio of first to second oxidation dye precursor is about equimolar.

15. The composition of claim 12 wherein said second oxidation dye precursor is present and the mol ratio of first to second oxidation dye precursor is about equimolar.

16. The composition of claim 1 wherein said second oxidation dye precursor is present in about an equimolar amount to said first dye precursor.

17. The composition of claim 1 wherein the combined oxidation dye precursors are present in about 0.2 to 5% by weight, based on the weight of the entire composition.

18. The composition of claim 13 wherein the combined oxidation dye precursors are present in about 0.2 to 5% by weight, based on the weight of the entire composition.

19. The composition of claim 14 wherein the combined oxidation dye precursors are present in about 0.2 to 5% by weight, based on the weight of the entire composition.

20. The composition of claim 15 wherein the combined oxidation dye precursors are present in about 0.2 to 5% by weight, based on the weight of the entire composition.

21. The composition of claim 1 wherein the combined oxidation dye precursors are present in about 1 to 3% by weight, based on the weight of the entire composition.

22. The composition of claim 13 wherein the combined oxidation dye precursors are present in about 1 to 3% by weight, based on the weight of the entire composition.

23. The composition of claim 14 wherein the combined oxidation dye precursors are present in about 1 to 3% by weight, based on the weight of the entire composition.

24. The composition of claim 15 wherein the combined oxidation dye precursors are present in about 1 to 3% by weight, based on the weight of the entire composition.

25. The composition of claim 1 wherein said first oxidation dye precursor is present in about 0.05 to 10 millimoles per 100 g of the total composition.

26. The composition of claim 13 wherein said first oxidation dye precursor is present in about 0.05 to 10 millimoles per 100 g of the total composition.

27. The composition of claim 14 wherein said first oxidation dye precursor is present in about 0.05 to 10 millimoles per 100 g of the total composition.

28. The composition of claim 15 wherein said first oxidation dye precursor is present in about 0.05 to 10 millimoles per 100 g of the total composition.

29. A method for the treatment of human hair comprising: applying the composition of claim 1 in a hair dyeing effective amount, at a temperature of about 15° C. to 40° C. and for a time of about 20 to 40 minutes; and then substantially removing any of said composition which is not fixed to said hair.

30. A method for the treatment of human hair comprising: applying the composition of claim 13 in a hair dyeing effective amount, at a temperature of about 15° C. to 40° C. and for a time of about 20 to 40 minutes; and then substantially removing any of said composition which is not fixed to said hair.

31. A method for the treatment of human hair comprising: applying the composition of claim 14 in a hair dyeing effective amount, at a temperature of about 15° C. to 40° C. and for a time of about 20 to 40 minutes; and then substantially removing any of said composition which is not fixed to said hair.

32. A method for the treatment of human hair comprising: applying the composition of claim 15 in a hair dyeing effective amount, at a temperature of about 15° C. to 40° C. and for a time of about 20 to 40 minutes; and then substantially removing any of said composition which is not fixed to said hair.

33. An aminodiphenylamine of the formula:

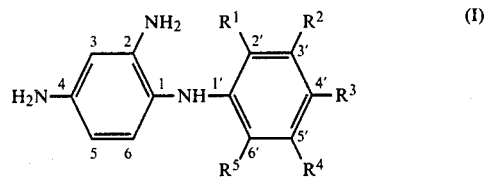

wherein $R^1$ through $R^5$ have one of the following substituent combinations:

| Combination | $R^1$ | $R^2$ | $R^3$ | $R^4$ | $R^5$ |
|---|---|---|---|---|---|
| a | COOH | H | CH$_3$ | H | H |
| b | H | COOH | H | H | CH$_3$ |
| c | H | COOH | H | H | CH$_3$O |
| d | COOH | H | H | H | CH$_3$ |
| e | COOH | CH$_3$ | H | H | H |
| f | COOH | H | H | Cl | H |
| g | H | H | CH$_2$COOH | H | H | or its salt.

34. The amino diphenylamine of claim 33 wherein
(a) is a trihydrochloride,
(b) is a trihydrochloride,
(c) is a dihydrochloride dihydrate,
(d) is a dihydrochloride dihydrate,
(e) is a dihydrochloride dihydrate,
(f) is a dihydrochloride dihydrate, and
(g) is a dihydrochloride.

* * * * *